(12) United States Patent
Schmiedel

(10) Patent No.: US 7,041,244 B2
(45) Date of Patent: May 9, 2006

(54) METHOD FOR PRODUCING MOULDED BODIES

(75) Inventor: Peter Schmiedel, Duesseldorf (DE)

(73) Assignee: Henkel Kommanditgesellschaft auf Aktien (Henkel KGaA), Duesseldorf (DE)

( * ) Notice: Subject to any disclaimer, the term of this patent is extended or adjusted under 35 U.S.C. 154(b) by 308 days.

(21) Appl. No.: 10/220,719

(22) PCT Filed: Feb. 23, 2001

(86) PCT No.: PCT/EP01/02074

§ 371 (c)(1),
(2), (4) Date: Sep. 4, 2002

(87) PCT Pub. No.: WO01/66684

PCT Pub. Date: Sep. 13, 2001

(65) Prior Publication Data

US 2003/0062646 A1 Apr. 3, 2003

(30) Foreign Application Priority Data

Mar. 4, 2000 (DE) .......................... 100 10 759

(51) Int. Cl.
*C11D 17/00* (2006.01)
*A61K 9/20* (2006.01)
*C05G 5/00* (2006.01)
*A01N 25/34* (2006.01)

(52) U.S. Cl. .................. 264/71; 264/82; 264/109; 264/112; 264/113; 264/123; 71/64.13; 424/464; 424/472; 510/224

(58) Field of Classification Search ............ 264/71, 264/82, 83, 109, 112, 113, 123; 510/224; 424/464, 472; 71/64.13
See application file for complete search history.

(56) References Cited

U.S. PATENT DOCUMENTS

| 3,234,258 A | 2/1966 | Morris |
| 3,489,687 A | 1/1970 | Inamorato et al. |
| 5,075,041 A | 12/1991 | Lutz |

FOREIGN PATENT DOCUMENTS

| CA | 2 053 900 | 10/1990 |
| JP | 55 167039 | 12/1980 |
| JP | 57 184491 | 11/1982 |
| JP | 58 217598 | 12/1983 |
| JP | 61 176519 | 8/1986 |
| WO | WO 90/13533 | 11/1990 |
| WO | WO 95/07976 | 3/1995 |

OTHER PUBLICATIONS

Database WPI Section Ch, Week 198638, AN1986–248712 XP002174367 of JP 61 176519 dated Aug. 8, 1986.
Database WPI Section Ch, Week 198251, AN1982–10378J XP002174368 of JP 57 184491 dated Nov. 13, 1982.
Database WPI Section Ch, Week 198110, AN1981–16266D XP002174369 of JP 55 167039 dated Dec. 26, 1980.

*Primary Examiner*—Mary Lynn Theisen
(74) *Attorney, Agent, or Firm*—Glenn E. I. Murphy; John E. Drach

(57) ABSTRACT

A process for producing tablets comprising one or more active substances, in which pulverulent to granular starting components are shaped and then solidified, wherein the solidification takes place by reacting a component A and a component B with one another, components A and B being mixed with the starting components, applied to them or added after shaping.

29 Claims, No Drawings

METHOD FOR PRODUCING MOULDED BODIES

CROSS-REFERENCE TO RELATED APPLICATIONS

This application is a U.S. National Stage application filed under 35 U.S.C. § 371, claiming priority of International Application No. PCT/EP01/02074, filed Feb. 23, 2001 in the European Patent Office, and DE 100 10 759.1, filed Mar. 4, 2000 in the German Patent Office, under 35 U.S.C. §§ 119 and 365.

BACKGROUND OF THE INVENTION

The present invention relates to a process for producing tablets, for example, for producing laundry and other detergent tablets, tablets for producing aqueous binder systems (wallpaper paste tablet), tablets for pharmaceutical or cosmetic applications or tablets for the agricultural sector, comprising one or more active substances, in which the starting components are shaped and then solidified.

Tablets, also referred to as shaped bodies, are a widely used product form in pharmacy and in chemical technology. They are normally composed of one or more active substances (e.g., drug) and, if desired, additions of fillers, binders, and lubricants. Another field of use is that of laundry and other detergents.

The tableted products have a number of advantages over the originally unshaped constituents: they are easier to dose and to handle and owing to their compact structure have advantages in storage and during transportation. The tablets are generally produced in special tableting machines, using eccentric and rotary presses. The unformed starting constituents, frequently powders, are either compressed directly or else granulated beforehand in order to improve the flow properties and adhesion properties of the starting components.

The production of tablets using tableting machines is very complicated, since pressure-sensitive components in particular can only be used to a restricted extent. Another possibility for producing tablets is to process the ingredients in the form of melts, e.g., to use a meltable material as matrix material for the other ingredients and then to shape the melt. Processing in a melt also has the disadvantage that temperature-sensitive ingredients can be incorporated only to a small extent, if at all. Moreover, the disintegration characteristics of tablets produced in this way are often unsatisfactory.

The object on which the present invention is based was to provide a simple process for producing tablets, especially laundry and other detergent tablets, tablets for producing binder systems or tablets for cosmetic applications, and also for the agricultural sector, in which the tablets can be obtained with almost no thermal or pressure load.

DESCRIPTION OF THE INVENTION

The present invention provides a process for producing tablets comprising one or more active substances, in which the starting components are shaped and then solidified, which is characterized in that the solidification takes place by reacting a component A and a component B with one another, components A and B being mixed with the starting components, applied to them or added after shaping.

As the process of the invention is being carried out, components A and B react with one another, with solidification of the individual ingredients. The reaction product formed from the components A and B joins the individual starting components in such a way as to give a solid, relatively fracture-stable tablet.

Using the process of the invention, tablets with effective disintegration are obtained. Since the binding of the individual ingredients takes place by reactive sintering and is not due to the "stickiness" of the granules of the premix, it is not necessary to adapt the formula to the binding properties of the individual ingredients. These can be adapted as desired depending on their effectiveness.

In order to react the components A and B with one another, it has proven advantageous if the starting components are mixed with component A or are coated with it before being shaped. Examples of compounds of component A are the alkali metal hydroxides, especially NaOH and KOH, alkaline earth metal hydroxides, especially $Ca(OH)_2$, alkali metal silicates organic or inorganic acids, such as citric acid, or acidic salts such as hydrogen sulfate, anhydrous hydratable salts or salts containing water of hydration, such as sodium carbonate, acetates, sulfates, alkali metal metallates, where the compounds mentioned above, where possible, can also be employed in the form of their aqueous solutions.

Component B is selected such that it reacts with component A without exerting relatively high pressures or substantially increasing the temperature, the reaction being accompanied by formation of a solid and solidification of the other starting components present. Examples of compounds of component B are $CO_2$, $NH_3$, water vapor or spray mist, salts containing water of hydration, which may react by hydrate migration with the anhydrous salts present as component A, anhydrous salts which form hydrates, which react with hydrate migration with the salts of component A containing water of hydration, and also $SO_2$, $SO_3$, HCl, HBr.

The abovementioned components A and B are interchangeable, provided two components are used which react with one another with sintering.

In one preferred embodiment of the present invention, the starting components are mixed or coated with compounds of component A and then the compounds of component B are added. It has proven particularly suitable if the compounds of component B are gaseous. The shaped starting components (referred to below as preforms) can then either be gassed in simple form or introduced into a gas atmosphere. One particularly preferred combination of components A and B are alkali metal hydroxides, especially NaOH and KOH, alkaline earth metal hydroxides, or alkali metal silicates, which are preferably used in the form of aqueous solutions, as component A and $CO_2$ as component B.

To carry out the process of the invention, the starting components are first shaped, i.e., they are customarily introduced into a die which has the external shape of the tablet to be produced. The starting components are preferably in pulverulent to granular form. They are first of all mixed with component A or coated with it. After being introduced into the die or tableting mold, it has proven preferable to apply slight pressure to the starting components in the die, e.g., by hand or using a ram, at a pressure of up to 1 kN. It is also possible to compact the premix by vibration (tapping compaction).

Where component A is not already in the form of a mixture with the starting components, the components are then coated with it, and component B is added. After the reaction has taken place, a fracture-stable tablet is obtained without the action of pressure or temperature.

Where one of the components, A or B, is a gas, it can be added, for example, to a preform, so that the gas flows through it. This procedure permits uniform hardening of the tablet within a short time.

In a further process variant, a preform is introduced into an atmosphere of the reactive gas. This variant is easy to carry out. It is possible to produce tablets which have a hardness gradient, i.e., tablets having only a hardened surface through to tablets which are completely hardened.

A preform or the premix can also be reacted with the reactive gas under superatmospheric pressure. This process variant has the advantage that the surface hardens rapidly to form a hard shell, the hardening process being stopped here or, as described above, fully hardened tablets can also be produced by way of increasing hardening stages.

The above process variants can also be combined, by firstly passing reactive gas through the preform in order to expel air. The preform is then exposed to a gas atmosphere at atmospheric pressure. As a result of the reaction between the gas and the second component, gas is automatically drawn into the preform by suction.

In one possible embodiment of the present invention, not the starting mixture but instead an already shaped preform is coated with component A and then reacted with component B. It hardens the layer on the surface of the preform, while in the core the loose or slightly compacted structure is retained. Tablets of this kind are notable for particularly good disintegration characteristics.

The strength of the tablets produced in accordance with the invention can be adjusted through a suitable selection of components A and B and also through the amount of these components that is employed. Moreover, the tablets may comprise binders, although their use is not preferred. Suitable binders include a large number of tablet binders known from pharmacy. They differ in their hydrophilicity/hydrophobicity, their solubility, and, resulting therefrom, in their binder effect. In particular it is possible to use substances from the group of the polyalkylene glycols and polyoxyalkylene glycols of different molecular weight. Those which have been found particularly suitable are [lacuna]. In addition, other substances as well are suitable, such as waxes, paraffins, fatty acid salts (soaps), especially stearates; fatty acids and fatty alcohols, fatty acid esters, cellulose derivatives, hydrocolloids, mono-, oligo-, or polysaccharides, and polymeric compounds (e.g. polyacrylates) and resins, for example.

In order to accelerate the subsequent disintegration of the tablets in use, they may optionally comprise what are known as tablet disintegrants. A great advantage of the tablets produced by the process of the invention, however, is that good disintegration results can be achieved even without the use of a disintegrant or with a smaller amount, in comparison to compressed tablets of equal hardness.

The tablets produced in accordance with the invention may be utilized for a host of applications. The starting components are selected in dependence on the chosen application. Possible applications that may be mentioned include laundry detergents, cleaning products, especially detergents for machine but also hand dishwashing, tablets for cosmetic applications, wallpaper paste tablets, and tablets for use in agriculture (pesticides, herbicides, etc.).

The process of the invention allows the production of single-phase and multiphase tablets which may have any desired shape. For the production of multiphase tablets it has proven advantageous first to produce a preform from one phase. Subsequently, one or more further phases can be applied. The phases may differ through different ingredients and also only through their coloration. By means of this procedure, in particular by the amount of component A employed in the respective phases, it is possible to produce phases differing in hardness and disintegration time, so that their active substances can be released sequentially in a controlled way during use.

In another embodiment, the tablets of the invention have a cavity which can be filled appropriately. Suitable fillings for the cavity include, for example, a solidifying melt or else powder, it being possible to fasten the powder in the cavity by means of a coating layer. The ingredients preferably incorporated into the cavity are substances which during the use of the tablets can be released, where appropriate, at a later or earlier point in time than the ingredients of the sintered tablet part.

In addition to the metered introduction of a melt, it is also possible to assemble one or more cores prepared otherwise beforehand, preferably by a noncompressive method, which may be of any design, e.g., sphere, ellipsoid, lens. The assembly can take place by adhesively bonding the core into the hardened tablet or introducing it into the preform and joining it to it in frictional or positively connected form during the hardening phase. The core here need not necessarily be visible on the surface of the tablet. It may also be present fully below the surface or exactly in the center of the sintered tablet.

It is also possible for the core to be placed loosely in the cavity on the surface of the tablet, which has preferably already undergone curing, and to be fixed by overcasting with an adhesive or a melt, e.g., a waxlike substance, such as paraffin, PEG, etc.

In one preferred embodiment, the tablet produced in accordance with the invention is a machine dishwashing detergent or laundry detergent. In this embodiment, the active substances are preferably selected from builder materials, surfactants, bleaches, bleach activators, enzymes, enzyme stabilizers, corrosion inhibitors, scale inhibitors, complexing agents, inorganic salts, graying inhibitors, foam inhibitors, silicone oils, soil release compounds, color transfer inhibitors, salts of polyphosphonic acids, optical brighteners, fluorescence agents, disinfectants, fragrances, dyes, antistats, easy-iron agents, repellants and impregnants, swelling and nonslip agents, UV absorbers or mixtures thereof.

As builder materials it is possible to use all of the builder substances known in the field of laundry detergents and cleaning products, especially the zeolites, silicates, carbonates, phosphates, and also organic cobuilders.

Suitable crystalline, layered sodium silicates possess the general formula NaMSi$_x$O$_{2x+1}$·yH$_2$O, where m is sodium or hydrogen, x is a number from 1.9 to 4 and y is a number from 0 to 20, and preferred values for x are 2, 3 or 4. Preferred crystalline phyllosilicates of the formula indicated are those in which M is sodium and x adopts the value 2 or 3. In particular, both β- and δ-sodium disilicates Na$_2$Si$_2$O$_5$·yH2O are preferred.

It is also possible to use amorphous sodium silicates having an Na$_2$O:SiO$_2$ modulus of from 1:2 to 1:3.3, preferably from 1:2 to 1:2.8, and in particular from 1:2 to 1:2.6, which are dissolution-retarded and have secondary washing properties. The retardation of dissolution relative to conventional amorphous sodium silicates may have been brought about in a variety of ways—for example, by surface treatment, compounding, compacting, or overdrying. In the context of this invention, the term "amorphous" also embraces "X-ray-amorphous". This means that in X-ray diffraction experiments the silicates do not yield the sharp X-ray reflections typical of crystalline substances but instead yield at best one or more maxima of the scattered X-radiation, having a width of several degree units of the diffraction angle. However, good builder properties may result, even particularly good builder properties, if the silicate particles in electron diffraction experiments yield vague or even sharp diffraction maxima. The interpretation of this is that the products have microcrystalline regions with a size of from 10 to several hundred nm, values up to max. 50 nm and in particular up to max. 20 nm being preferred. Particular preference is given to compacted amorphous silicates, compounded amorphous silicates, and over-dried X-ray-amorphous silicates.

The finely crystalline, synthetic zeolite used, containing bound water, is preferably zeolite A and/or P. A particularly preferred zeolite P is Zeolite MAP® (commercial product from Crosfield). Also suitable, however, are zeolite X and also mixtures of A, X and/or P. Another product available commercially and able to be used with preference in the context of the present invention, for example, is a cocrystallizate of zeolite X and zeolite A (approximately 80% by weight zeolite X), which is sold by CONDEA Augusta S.p.A. under the brand name VEGOBOND AX® and may be described by the formula

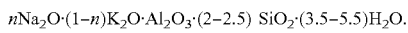
$n\text{Na}_2\text{O} \cdot (1-n)\text{K}_2\text{O} \cdot \text{Al}_2\text{O}_3 \cdot (2-2.5) \text{ SiO}_2 \cdot (3.5-5.5)\text{H}_2\text{O}$.

Suitable zeolites have an average particle size of less than 10 μm (volume distribution; measurement method: Coulter counter) and contain preferably from 18 to 22% by weight, in particular from 20 to 22% by weight, of bound water.

Of course, the widely known phosphates may also be used as builder substances. Among the large number of commercially available phosphates, the alkali metal phosphates, with particular preference being given to pentasodium and pentapotassium triphosphate (sodium and potassium tripolyphosphate, respectively), possess the greatest importance in the detergents industry.

Organic cobuilders which may be used in the machine dishwashing compositions of the invention are, in particular, polycarboxylates/polycarboxylic acids, polymeric polycarboxylates, aspartic acid, polyacetals, dextrins, further organic cobuilders (see below), and phosphonates. These classes of substance are described below.

Organic builder substances which are suitable are, for example, the polycarboxylic acids usable in the form of their sodium salts, the term polycarboxylic acids meaning those carboxylic acids which carry more than one acid function. Examples of these are citric acid, adipic acid, succinic acid, glutaric acid, malic acid, tartaric acid, maleic acid, fumaric acid, sugar acids, amino carboxylic acids, nitrilotriacetic acid (NTA), provided such use is not objectionable on ecological grounds, and also mixtures thereof. Preferred salts are the salts of the polycarboxylic acids such as citric acid, adipic acid, succinic acid, glutaric acid, tartaric acid, sugar acids, and mixtures thereof.

The acids per se may also be used. In addition to their builder effect, the acids typically also possess the property of an acidifying component and thus also serve to establish a lower pH of detergents. In this context, mention may be made in particular of citric acid, succinic acid, glutaric acid, adipic acid, gluconic acid, and any desired mixtures thereof.

Also suitable as builders are polymeric polycarboxylates; these are, for example, the alkali metal salts of polyacrylic acid or of polymethacrylic acid, examples being those having a relative molecular mass of from 500 to 70 000 g/mol.

The molecular masses reported for polymeric polycarboxylates, for the purposes of this document, are weight-average molecular masses, $M_w$, of the respective acid form, determined basically by means of gel permeation chromatography (GPC) using a UV detector. The measurement was made against an external polyacrylic acid standard, which owing to its structural similarity to the polymers under investigation provides realistic molecular weight values. These figures differ markedly from the molecular weight values obtained using polystyrenesulfonic acids as the standard. The molecular masses measured against polystyrenesulfonic acids are generally much higher than the molecular masses reported in this document.

Suitable polymers are, in particular, polyacrylates, which preferably have a molecular mass of from 2 000 to 20 000 g/mol. Owing to their superior solubility, preference in this group may be given in turn to the short-chain polyacrylates, which have molecular masses of from 2 000 to 10 000 g/mol, and with particular preference from 3 000 to 5 000 g/mol.

Also suitable are copolymeric polycarboxylates, especially those of acrylic acid with methacrylic acid and of acrylic acid or methacrylic acid with maleic acid. Copolymers which have been found particularly suitable are those of acrylic acid with maleic acid which contain from 50 to 90% by weight of acrylic acid and from 50 to 10% by weight of maleic acid. Their relative molecular mass, based on free acids, is generally from 2 000 to 70 000 g/mol, preferably from 20 000 to 50 000 g/mol, and in particular from 30 000 to 40 000 g/mol.

The (co)polymeric polycarboxylates can be used either as powders or as aqueous solutions. The (co)polymeric polycarboxylate content of the compositions is preferably from 0.5 to 20% by weight, in particular from 3 to 10% by weight.

In order to improve the solubility in water, the polymers may also contain allylsulfonic acids, such as allyloxybenzenesulfonic acid and methallylsulfonic acid, for example, as monomers.

Particular preference is also given to biodegradable polymers comprising more than two different monomer units, examples being those comprising, as monomers, salts of acrylic acid and of maleic acid, and also vinyl alcohol or vinyl alcohol derivatives, or those comprising, as monomers, salts of acrylic acid and of 2-alkylallylsulfonic acid, and also sugar derivatives.

Further preferred copolymers are those whose monomers are preferably acrolein and acrylic acid/acrylic acid salts, and, respectively, acrolein and vinyl acetate.

Similarly, further preferred builder substances that may be mentioned include polymeric amino dicarboxylic acids, their salts or their precursor substances, examples being polyaspartic acids and their salts and derivatives.

Further suitable builder substances are polyacetals, which may be obtained by reacting dialdehydes with polyol carboxylic acids having 5 to 7 carbon atoms and at least 3 hydroxyl groups. Preferred polyacetals are obtained from dialdehydes such as glyoxal, glutaraldehyde, terephthalaldehyde and mixtures thereof and from polyol carboxylic acids such as gluconic acid and/or glucoheptonic acid.

Further suitable organic builder substances are dextrins, examples being oligomers and polymers of carbohydrates, which may be obtained by partial hydrolysis of starches. The hydrolysis can be conducted by customary processes; for example, acid-catalyzed or enzyme-catalyzed processes. The hydrolysis products preferably have average molecular masses in the range from 400 to 500 000 g/mol. Preference is given here to a polysaccharide having a dextrose equivalent (DE) in the range from 0.5 to 40, in particular from 2 to 30, DE being a common measure of the reducing effect of a polysaccharide in comparison to dextrose, which possesses a DE of 100. It is possible to use both maltodextrins having a DE of between 3 and 20 and dried glucose syrups having a DE of between 20 and 37, and also so-called yellow dextrins and white dextrins having higher molecular masses, in the range from 2 000 to 30 000 g/mol.

The oxidized derivatives of such dextrins comprise their products of reaction with oxidizing agents which are able to oxidize at least one alcohol function of the saccharide ring to the carboxylic acid function. A product oxidized at $C_6$ of the saccharide ring may be particularly advantageous.

Oxydisuccinates and other derivatives of disuccinates, preferably ethylenediamine disuccinate, are further suitable cobuilders. Ethylenediamine N,N'-disuccinate (EDDS) is used preferably in the form of its sodium or magnesium salts. Further preference in this context is given to glycerol disuccinates and glycerol trisuccinates as well. Suitable use amounts in formulations containing zeolite and/or silicate are from 3 to 15% by weight.

Examples of further useful organic cobuilders are acetylated hydroxy carboxylic acids and their salts, which may also, if desired, be present in lactone form and which contain at least 4 carbon atoms, at least one hydroxyl group, and not more than two acid groups.

A further class of substance having cobuilder properties is represented by the phosphonates. The phosphonates in question are, in particular, hydroxyalkane- and aminoalkanephosphonates. Among the hydroxyalkanephosphonates, 1-hydroxyethane-1,1-diphosphonate (HEDP) is of particular importance as a cobuilder. It is used preferably as the sodium salt, the disodium salt being neutral and the tetrasodium salt giving an alkaline (pH 9) reaction. Suitable aminoalkanephosphonates are preferably ethylenediaminetetramethylenephosphonate (EDTMP), diethylenetriaminepentamethylenephosphonate (DTPMP), and their higher homologs. They are used preferably in the form of the neutrally reacting sodium salts, e.g., as the hexasodium salt of EDTMP or as the hepta- and octa-sodium salt of DTPMP. As a builder in this case, preference is given to using HEDP from the class of the phosphonates. Furthermore, the aminoalkanephosphonates possess a pronounced heavy metal binding capacity. Accordingly, and especially if the compositions also contain bleach, it may be preferred to use aminoalkanephosphonates, especially DTPMP, or to use mixtures of said phosphonates.

Furthermore, all compounds capable of forming complexes with alkaline earth metal ions may be used as cobuilders.

Suitable surfactants include in particular the anionic and nonionic surfactants. Whereas normally only low-foaming nonionic surfactants are used in machine dishwashing detergents, laundry detergents generally also include anionic surfactants and also, in small amounts, ampholytic and zwitterionic surfactants as well.

Nonionic surfactants used are preferably alkoxylated, advantageously ethoxylated, especially primary, alcohols having preferably 8 to 18 carbon atoms and on average from 1 to 12 mol of ethylene oxide (EO) per mole of alcohol, in which the alcohol radical may be linear or, preferably, methyl-branched in position 2 and/or may comprise linear and methyl-branched radicals in a mixture, as are commonly present in oxo alcohol radicals. In particular, however, preference is given to alcohol ethoxylates containing linear radicals from alcohols of natural origin having 12 to 18 carbon atoms, e.g., from coconut, palm, tallow fatty or oleyl alcohol and on average from 2 to 8 EO per mole of alcohol. Preferred ethoxylated alcohols include, for example, $C_{12-14}$ alcohols containing 3 EO or 7 EO, $C_{9-11}$ alcohol containing 7 EO, $C_{13-15}$ alcohols containing 3 EO, 5 EO, 7 EO or 8 EO, $C_{12-18}$ alcohols containing 3 EO, 5 EO or 7 EO, and mixtures thereof, such as mixtures of $C_{12-14}$ alcohol containing 3 EO and $C_{12-18}$ alcohol containing 7 EO. The stated degrees of ethoxylation represent statistical mean values, which for a specific product may be an integer or a fraction. Preferred alcohol ethoxylates have a narrowed homolog distribution (narrow range ethoxylates, NRES). In addition to these nonionic surfactants it is also possible to use fatty alcohols containing more than 12 EO. Examples thereof are tallow fatty alcohol containing 14 EO, 25 EO, 30 EO or 40 EO. Nonionic surfactants containing EO and PO groups together in the molecule can also be used in accordance with the invention. In this context it is possible to use block copolymers containing EO-PO block units and PO-EO block units, and also EO-PO-EO copolymers and PO-EO-PO copolymers. Of course, it is also possible to use nonionic surfactants with mixed alkoxylation, in which EO units and PO units are distributed not in blocks but randomly. Such products are obtainable by simultaneous action of ethylene oxide and propylene oxide on fatty alcohols.

As further nonionic surfactants, furthermore, use may also be made of alkyl glycosides of the general formula $RO(G)_x$, where R is a primary straight-chain or methyl-branched aliphatic radical, especially an aliphatic radical methyl-branched in position 2, containing 8 to 22, preferably 12 to 18, carbon atoms, and G is the symbol representing a glycose unit having 5 or 6 carbon atoms, preferably glucose. The degree of oligomerization, x, which indicates the distribution of monoglycosides and oligoglycosides, is any desired number between 1 and 10; preferably, x is from 1.2 to 1.4.

A further class of nonionic surfactants used with preference are alkoxylated, preferably ethoxylated, or ethoxylated and propoxylated, fatty acid alkyl esters, preferably having 1 to 4 carbon atoms in the alkyl chain, especially fatty acid methyl esters, as described, for example, in Japanese patent application JP 58/217598 or preferably prepared by the process described in international patent application WO-A-90/13533.

Nonionic surfactants of the amine oxide type, examples being N-cocoalkyl-N,N-dimethylamine oxide and N-tallowalkyl-N,N-dihydroxyethylamine oxide, and of the fatty acid alkanolamide and fatty amine alkoxylate type, may also be suitable. The amount of these nonionic surfactants is preferably not more than that of the ethoxylated fatty alcohols, in particular not more than half thereof.

Further suitable surfactants are polyhydroxy fatty acid amides of the formula I

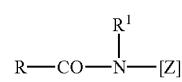

where RCO is an aliphatic acyl radical having 6 to 22 carbon atoms, $R^1$ is hydrogen or an alkyl or hydroxyalkyl radical having 1 to 4 carbon atoms, and [Z] is a linear or branched polyhydroxyalkyl radical having 3 to 10 carbon atoms and from 3 to 10 hydroxyl groups. The polyhydroxy fatty acid amides are known substances which are customarily obtainable by reductive amination of a reducing sugar with ammonia, an alkylamine or an alkanolamine, and subsequent acylation with a fatty acid, a fatty acid alkyl ester or a fatty acid chloride.

The group of the polyhydroxy fatty acid amides also includes compounds of the formula II

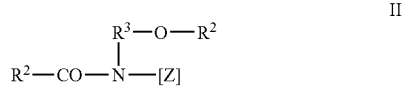

where $R^2$ is a linear or branched alkyl or alkenyl radical having 7 to 12 carbon atoms, $R^3$ is a linear, branched or cyclic alkyl radical or an aryl radical having 2 to 8 carbon atoms and $R^4$ is a linear, branched or cyclic alkyl radical or an aryl radical or an oxyalkyl radical having 1 to 8 carbon atoms, preference being given to $C_{1-4}$ alkyl radicals or phenyl radicals, and [Z] is a linear polyhydroxyalkyl radical whose alkyl chain is substituted by at least two hydroxyl groups, or alkoxylated, preferably ethoxylated or propoxylated, derivatives of said radical.

[Z] is preferably obtained by reductive amination of a sugar, e.g., glucose, fructose, maltose, lactose, galactose, mannose or xylose.

Anionic surfactants used are, for example, those of the sulfonate and sulfate type. Preferred surfactants of the sulfonate type are $C_{9-13}$ alkylbenzenesulfonates, olefinsulfonates, i.e., mixtures of alkenesulfonates and hydroxyalkanesulfonates, and also disulfonates, as are obtained, for example, from $C_{12-18}$ monoolefins having a terminal or internal double bond by sulfonating with gaseous sulfur trioxide followed by alkaline or acidic hydrolysis of the sulfonation products. Also suitable are alkanesulfonates, which are obtained from $C_{12-18}$ alkanes, for example, by sulfochlorination or sulfoxidation with subsequent hydrolysis or neutralization, respectively. Likewise suitable, in addition, are the esters of α-sulfo fatty acids (ester sulfonates), e.g., the α-sulfonated methyl esters of hydrogenated coconut, palm kernel or tallow fatty acids.

Preferred alk(en)yl sulfates are the alkali metal salts, and especially the sodium salts, of the sulfuric monoesters of $C_{12}$–$C_{18}$ fatty alcohols, examples being those of coconut fatty alcohol, tallow fatty alcohol, lauryl, myristyl, cetyl or stearyl alcohol, or of $C_{10}$–$C_{20}$ oxo alcohols, and those monoesters of secondary alcohols of these chain lengths. Preference is also given to alk(en)yl sulfates of said chain length which contain a synthetic straight-chain alkyl radical prepared on a petrochemical basis. From a detergents standpoint, the $C_{12}$–$C_{16}$ alkyl sulfates and $C_{12}$–$C_{15}$ alkyl sulfates, and also $C_{14}$–$C_{15}$ alkyl sulfates, are preferred. In addition, 2,3-alkyl sulfates, which are prepared for example as per U.S. Pat. Nos. 3,234,258 or 5,075,041 and may be obtained as commercial products from Shell Oil Company under the name DAN®, are suitable anionic surfactants.

Further suitable anionic surfactants are sulfated fatty acid glycerol esters. Fatty acid glycerol esters are the monoesters, diesters and triesters, and mixtures thereof, as obtained in the preparation by esterification of a monoglycerol with from 1 to 3 mol of fatty acid or in the transesterification of triglycerides with from 0.3 to 2 mol of glycerol. Preferred sulfated fatty acid glycerol esters are the sulfation products of saturated fatty acids having 6 to 22 carbon atoms, examples being those of caproic acid, caprylic acid, capric acid, myristic acid, lauric acid, palmitic acid, stearic acid, or behenic acid.

Also suitable are the sulfuric monoesters of the straight-chain or branched $C_{7-21}$ alcohols ethoxylated with from 1 to 6 mol of ethylene oxide, such as 2-methyl-branched $C_{9-11}$ alcohols containing on average 3.5 mol of ethylene oxide (EO) or $C_{12-18}$ fatty alcohols containing from 1 to 4 EO. Because of their high foaming behavior they are used in surfactant compositions or detergents only in relatively small amounts, for example, in amounts of from 1 to 5% by weight.

Further suitable anionic surfactants include the salts of alkylsulfosuccinic acid, which are also referred to as sulfosuccinates or as sulfosuccinic esters and which constitute monoesters and/or diesters of sulfosuccinic acid with alcohols, preferably fatty alcohols and especially ethoxylated fatty alcohols. Preferred sulfosuccinates comprise $C_{8-18}$ fatty alcohol radicals or mixtures thereof. Especially preferred sulfosuccinates contain a fatty alcohol radical derived from ethoxylated fatty alcohols which themselves represent nonionic surfactants (for description, see below). Particular preference is given in turn to sulfosuccinates whose fatty alcohol radicals are derived from ethoxylated fatty alcohols having a narrowed homolog distribution. Similarly, it is also possible to use alk(en)ylsuccinic acid having preferably 8 to 18 carbon atoms in the alk(en)yl chain, or salts thereof.

Further suitable anionic surfactants are, in particular, soaps. Suitable soaps include saturated and unsaturated fatty acid soaps, such as the salts of lauric acid, myristic acid, palmitic acid, stearic acid, hydrogenated erucic acid and behenic acid, and, in particular, mixtures of soaps derived from natural fatty acids, e.g., coconut, palm kernel, olive oil or tallow fatty acids.

The anionic surfactants, including the soaps, may, depending on pH, be present in the form of their sodium, potassium or ammonium salts and also as soluble salts of organic bases, such as mono-, di- or triethanolamine.

The zwitterionic surfactants are those surface-active compounds whose molecule carries at least one quaternary ammonium group and at least one $-COO^{(-)}$ or $-SO_3^{(-)}$ group. Particularly suitable zwitterionic surfactants are those known as betaines such as the N-alkyl-N,N-dimethylammonium glycinates, such as cocoalkyl-dimethylammonium glycinate, N-acyl-aminopropyl-N,N-dimethylammonium glycinates, for example cocoacylaminopropyl-dimethylammonium glycinate, and 2-alkyl-3-carboxymethyl-3-hydroxyethyl-imidazoline each having from 8 to 18 carbon atoms in the alkyl or acyl group, and also cocoacylaminoethylhydroxyethylcarboxy-methyl glycinate. A preferred zwitterionic surfactant is the fatty acid amide derivative known under the CTFA designation Cocamidopropyl Betaine.

Ampholytic surfactants are those surface-active compounds which in addition to a $C_{8-18}$ alkyl or acyl group in the molecule contain at least one free amino group and at least one $-COOH$ or $-SO_3H$ group and are capable of forming inner salts. Examples of suitable ampholytic surfactants are N-alkylglycines, N-alkyl-propionic acids, N-alkylaminobutyric acids, N-alkyl-iminodipropionic acids, N-hydroxyethyl-N-alkylamino-propylglycines, N-alkyltaurines, N-alkylsarcosines, 2-alkylaminopropionic acids and alkylaminoacetic acids each having from about 8 to 18 carbon atoms in the alkyl group. Particularly preferred ampholytic surfactants are N-cocoalkyl aminopropionate, cocoacyl-aminoethyl aminopropionate, and $C_{12-13}$ acylsarcosine.

Suitable examples of surfactants containing amino groups are the fatty amine alkoxylates.

Preferred bleaches are $H_2O_2$ and compounds which yield $H_2O_2$ in water, such as sodium perborate tetrahydrate, sodium perborate monohydrate, sodium percarbonate or corresponding percarbonate salts, persilicate, peroxypyrophosphates, such as monopersulfate, urea peroxyhydrate, citrate perhydrates, organic peroxides, and also $H_2O_2$-donating peracidic salts or peracids, such as perbenzoates, peroxophthalates, diperoxyazelaic acid, phthaloimino peracids or diperoxydodecanedioic acid. $H_2O_2$ is used with particular preference.

Further typical organic bleaches are the peroxy acids, particular examples being the alkyl peroxy acids and the aryl peroxy acids. Suitable representatives are dibenzoyl peroxide, peroxybenzoic acid and its ring-substituted derivatives, such as alkylperoxybenzoic acids, but also peroxy-α-naphthoic acid and magnesium monoperphthalate, (b) aliphatic or substituted aliphatic peroxy acids, such as peroxylauric acid, peroxystearic acid, ε-phthalimidoperoxycaproic acid [phthaloiminoperoxyhexanoic acid (PAP)], o-carboxybenzamidoperoxycaproic acid, N-nonenylamidoperadipic acid and N-nonenylamidopersuccinates, and (c) aliphatic and araliphatic peroxy dicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid and N,N-terephthaloyldi(6-aminopercaproic acid) may also be used.

Bleaches in the detergents of the invention for machine dishwashing may also be substances which release chlorine or bromine. Among the suitable chlorine- or bromine-releasing materials, examples include heterocyclic N-bromoamides and N-chloroamides, examples being trichloroisocyanuric acid, tribromoisocyanuric acid, dibromoisocyanuric acid and/or dichloroisocyanuric acid (DICA) and/or salts thereof with cations such as potassium and sodium. Hydantoin compounds, such as 1,3-dichloro-5,5-dimethylhydantoin, are likewise suitable.

Bleach activators which may be used are compounds which under perhydrolysis conditions give rise to aliphatic peroxo carboxylic acids having preferably 1 to 10 carbon atoms, in particular 2 to 4 carbon atoms, and/or substituted or unsubstituted perbenzoic acid. Suitable substances are those which carry O-acyl and/or N-acyl groups of the stated number of carbon atoms, and/or substituted or unsubstituted benzoyl groups. Preference is given to polyacylated alkylenediamines, especially tetraacetylethylenediamine (TAED), acylated triazine derivatives, especially 1,5-diacetyl-2,4-dioxohexa-hydro-1,3,5-triazine (DADHT), acylated glycolurils, especially tetraacetylglycoluril (TAGU), N-acylimides, especially N-nonanoylsuccinimide (NOSI), acylated phenolsulfonates, especially n-nonanoyl- or isononanoyloxybenzenesulfonate (n- or iso-NOBS), carboxylic anhydrides, especially phthalic anhydride, acylated polyhydric alcohols, especially triacetin, ethylene glycol diacetate, 2,5-diacetoxy-2,5-dihydro-furan, N-methylmorpholiniumacetonitrile methyl sulfate (MMA), and their enol esters and also acetylated sorbitol and mannitol and/or mixtures thereof (SORMAN), acylated sugar derivatives, especially pentaacetylglucose (PAG), pentaacetylfructose, tetraacetylxylose and octaacetyllactose, and acetylated, optionally N-alkylated glucamine and gluconolactone, and/or N-acylated lactams, for example, N-benzoylcaprolactam. Hydrophilically substituted acylacetals and acyllactams are likewise used with preference. Combinations of conventional bleach activators may also be used.

In addition to the conventional bleach activators, or instead of them, it is also possible for what are known as bleaching catalysts to be present. These substances are bleach-boosting transition metal salts or transition metal complexes such as, for example, Mn-, Fe-, Co-, Ru- or Mol-salen complexes or -carbonyl complexes. Other bleaching catalysts which can be used include Mn, Fe, Co, Ru, Mo, Ti, V and Cu complexes with N-containing tripod ligands, and also Co-, Fe-, Cu- and Ru-ammine complexes.

Suitable enzymes in the detergents of the invention include in particular those from the classes of the hydrolases such as the proteases, esterases, lipases or lipolytic enzymes, amylases, glycosyl hydrolases, and mixtures of said enzymes. All of these hydrolases contribute to removing stains, such as proteinaceous, fatty or starchy marks. For bleaching, it is also possible to use oxidoreductases. Especially suitable enzymatic active substances are those obtained from bacterial strains or fungi such as *Bacillus subtilis, Bacillus licheniformis, Streptomyceus griseus, Coprinus Cinereus* and *Humicola insolens*, and also from genetically modified variants thereof. Preference is given to the use of proteases of the subtilisin type, and especially to proteases obtained from *Bacillus lentus*. Of particular interest in this context are enzyme mixtures, examples being those of protease and amylase or protease and lipase or lipolytic enzymes, or of protease, amylase and lipase or lipolytic enzymes, or protease, lipase or lipolytic enzymes, but especially protease and/or lipase-containing mixtures or mixtures with lipolytic enzymes. Examples of such lipolytic enzymes are the known cutinases. Peroxidases or oxidases have also proven suitable in some cases. The suitable amylases include, in particular, alpha-amylases, iso-amylases, pullulanases, and pectinases.

The enzymes may be adsorbed on carrier substances or embedded in coating substances in order to protect them against premature decomposition. The proportion of the enzymes, enzyme mixtures or enzyme granules may be, for example, from about 0.1 to 5% by weight, preferably from 0.5 to about 4.5% by weight.

Dyes and fragrances may be added to the machine dishwashing compositions of the invention in order to enhance the esthetic appeal of the products which are formed and to provide the consumer with not only the performance but also a visually and sensorially "typical and unmistakable" product. As perfume oils and/or fragrances it is possible to use individual odorant compounds, examples being the synthetic products of the ester, ether, aldehyde, ketone, alcohol, and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate, and benzyl salicylate. The ethers include, for example, benzyl ethyl ether; the aldehydes include, for example, the linear alkanals having 8–18 carbon atoms, citral, citronellal, citronellyloxyacetaldehyde, cyclamen aldehyde, hydroxycitronellal, lilial and bourgeonal; the ketones include, for example, the ionones, α-isomethylionone and methyl cedryl ketone; the alcohols include anethole, citronellol, eugenol, geraniol, linalool, phenylethyl alcohol, and terpineol; the hydrocarbons include primarily the terpenes such as limonene and pinene. Preference, however, is given to the use of mixtures of different odorants, which together produce an appealing fragrance note. Such perfume oils may also contain natural odorant mixtures, as obtainable from plant sources, examples being pine oil, citrus oil, jasmine oil, patchouli oil, rose oil or ylang-ylang oil. Likewise suitable are muscatel, sage oil, camomile oil, clove oil, balm oil, mint oil, cinnamon leaf oil, lime blossom oil, juniperberry oil, vetiver oil, olibanum oil, galbanum oil and labdanum oil, and also orange blossom oil, neroli oil, orange peel oil, and sandalwood oil.

In order to enhance the esthetic appeal of the tablets produced in accordance with the invention, they (or parts thereof) may be colored with appropriate dyes. Preferred dyes, whose selection presents no difficulty whatsoever to the skilled worker, possess a high level of storage stability and insensitivity to the other ingredients of the compositions or to light and possess no pronounced affinity for the substrates to be treated with the compositions, such as glass, ceramic, or plasticware, or textiles, so as not to stain them.

Where the detergents prepared in accordance with the invention are used for machine dishwashing, they may include corrosion inhibitors for protecting the ware or the machine, with special importance being possessed, in particular, by silver protectants. In general it is possible to use, in particular, silver protectants selected from the group consisting of triazoles, benzotriazoles, bisbenzotriazoles, aminotriazoles, alkylaminotriazoles, and transition metal salts or transition metal complexes. Particular preference is given to the use of benzotriazole and/or alkylaminotriazole. Frequently encountered in cleaning formulations, furthermore, are agents containing active chlorine, which may significantly reduce corrosion of the silver surface. In chlorine-free cleaners, use is made in particular of oxygen-containing and nitrogen-containing organic redox-active compounds, such as divalent and trivalent phenols, e.g. hydroquinone, pyrocatechol, hydroxyhydroquinone, gallic acid, phloroglucinol, pyrogallol, and derivatives of these classes of compound. Inorganic compounds in the form of salts and complexes, such as salts of the metals Mn, Ti, Zr, Hf, V, Co and Ce, also find frequent application. Preference is given in this context to the transition metal salts selected from the group consisting of manganese and/or cobalt salts and/or complexes, with particular preference cobalt ammine complexes, cobalt acetate complexes, cobalt carbonyl complexes, the chlorides of cobalt or of manganese and manganese sulfate. Similarly, zinc compounds may be used to prevent corrosion on the ware.

In another preferred embodiment, the tablet produced in accordance with the invention is a machine dishwashing detergent which has a cavity. Into the cavity it is possible to introduce fillings (also referred to below as the core) which preferably comprise active substances which are not released until a wash or rinse cycle following the actual cleaning of the ware, preferably in the clear-rinse cycle.

In this embodiment, active substances present in the core include preferably one or more substances from the group consisting of surfactants, including rinse-aid surfactants, bleaches, bleach activators, corrosion inhibitors, scale inhibitors, fragrances and/or cobuilders; there is no intention to rule out the use of the other active substances mentioned above in the core.

It is also possible to incorporate fragrances into the core, leading to a sensation of fragrance when the machine is opened (see above).

In another preferred embodiment, the tablet of the invention is a laundry detergent which has a cavity. Into the cavity it is possible to introduce fillings which preferably comprise active substances which are not released until a wash cycle or rinse cycle after the actual washing of the textiles, preferably in a clear-rinse cycle. The active substances incorporated in the core preferably have textile care properties.

In this embodiment, active substances present in the core preferably include one or more substances from the group consisting of anionic, nonionic, cationic and/or amphoteric or zwitterionic surfactants, cationic and/or nonionic textile softeners, foam inhibitors, perfume oils, dyes, preservatives, soil release polymers, antistats and/or easy-iron agents; there is no intention to rule out the use of the other active substances mentioned above in the core.

The tablets produced in accordance with the invention may also be employed in the field of cosmetic or pharmaceutical products, in which case the starting substances constitute the active cosmetic or pharmaceutical substances. The process of the invention is likewise suitable for producing tablets for adhesives, especially water-based adhesives, such as wallpaper pastes. Further fields of use are all areas in which active substances have to be dosed, e.g., in agriculture and in horticulture, such as fertilizers and pesticides, herbicides, etc., compositions for water treatment, fuel tablets, and catalysts which are used in the form of shaped bodies.

EXAMPLES

Example 1

A laundry detergent tablet was produced as follows: First of all, granules of the following composition were prepared in a mixer:

| Ingredient | Proportion/% by wt. |
|---|---|
| ABS (Na salt) | 20 |
| C12–18 fatty alcohol + 7 EO | 6 |
| C12–18 fatty alcohol sulfate Na | 4 |
| Zeolite A | 30 |
| Sodium carbonate | 15 |
| Na silicate | 6 |
| Polycarboxylate | 5 |
| Water | 10 |
| Na sulfate | ad 100 |

After the granules have been dried in a fluidized-bed dryer to the stated water content and sieved off to particle sizes <0.8 mm, a mixture with the following composition was again prepared in the mixer:

| Ingredient | Proportion/% by wt. |
|---|---|
| Granules | 65 |
| Na percarbonate, coated | 15 |
| TAED | 6 |
| Enzyme granules | 3 |
| Standard auxiliaries (foam inhibitor granules, perfume oil, etc.) | 5 |
| Na sulfate | ad 100 |

This mixture was coated with 70% KOH in the mixer, so that 2% or 4% of pure KOH, based on the mixture, was present on the surfaces of the granules. The excess water is absorbed by the granules. 25 g of these coated granules were introduced into a die having a diameter of 40 mm and gently pressed down using a ram (100 N). $CO_2$ was then passed in a gentle stream through the die. The reaction can be monitored by measuring the temperature; the preform warms during the reaction to about 40° C. Exceedance of the temperature maximum on the underside of the tablet indicates the end of the reaction. In the case of the test setup used, this is the case after about 2–5 min. The preform can then be expressed from the die using a ram.

Example 2

A tablet for a machine dishwashing detergent was produced as follows:
First of all, a mixture of the following composition is prepared:

| Ingredient | Proportion/% by wt. |
|---|---|
| Na tripolyphosphate | 50 |
| Sodium carbonate | 15 |
| Na silicate | 5 |
| Polycarboxylate | 1 |
| Phosphonate | 1 |
| Nonionic surfactant | 2 |
| Na perborate monohydrate | 10 |
| TAED | 2 |
| Enzyme granules | 4 |
| Standard auxiliaries, water, salts | ad 100 |

After sieving off to <0.8 mm, this mixture was coated with 50% NaOH in a mixer, so that 5% or 7% of pure NaOH, based on the mixture, was present on the surface of the granules. 25 g of these coated granules were introduced into a die and gently pressed down using a ram (100 N). The subsequent procedure was as in example 1.

Example 3

A tablet for a machine dishwashing detergent with integrated rinse aid was produced as follows: First of all, the preform is prepared as in example 2 with the difference that the ram or the base of the die which are used for shaping possess a protrusion. Subsequently, the tablets are solidified as in the previous examples by introducing $CO_2$. Following withdrawal from the die, a tablet is obtained which has a cavity on one of its surfaces. Metered into this cavity is 1 g of a melt having the following composition:

| Ingredient | Proportion/% by wt. |
|---|---|
| Polytergent SLF 18 B 45 (Olin Chemicals) | 45 |
| Paraffin, m.p. 60–63° C. | 50 |
| Emulsifier | 5 |

Alternatively, a cast core of desired shape can be produced separately and mounted in the cavity.

What is claimed is:

1. A process for producing tablets comprising one or more active substances, in which pulverulant to granular starting components are shaped and then solidified, wherein the solidification takes place by reacting a component A and a component B with one another, components A and B being mixed with the starting components, applied to then or added after shaping.

2. The process of claim 1, wherein the starting components are mixed or coated with component A.

3. The process of claim 1, wherein component A is selected from the group consisting of alkali metal hydroxides, alkaline earth metal hydroxides, alkali metal silicates, organic or inorganic acids or acidic salts, anhydrous salts that form hydrates, and salts containing water of hydration.

4. The process of claim 1, wherein component B is selected from the group consisting of $CO_2$, $NH_2$, water vapor, salts containing water of hydration, anhydrous salts that form hydrates, $SO_2$, $SO_1$, HCl, and HBr.

5. The process of claim 1, wherein component A is selected from the group consisting of NaOH, KOH and $Ca(OR)_2$, and component B is $CO_2$.

6. The process of claim 1, wherein, after they have been shaped, the starting components are pressed down with a pressure of up to 1 kN or are compacted by vibration.

7. The process of claim 1, wherein component B comprises a gas and the gas flows through a preform or said preform is exposed to the gas under superatmospheric prosture, or is introduced into an atmosphere of the gas, or in that first of all the gas is caused to flow through the preform in order to expel air and the preform is then introduced into an atmosphere comprising the gas.

8. The process of claim 1, wherein single or multiphase tablets are produced.

9. The process of claim 8, wherein the individual phases have different hardness or disintegration times.

10. The process of claim 1, wherein the tablet is shaped with a cavity into which a filling can be introduced.

11. The process of claim 10, wherein the filling is incorporated in to a preform for the tablet and the filling solidifies in the cavity after the tablet is shaped.

12. The process of claim 1, wherein the tablet is a machine dishwashing detergent or laundry detergent.

13. The process of claim 1, wherein the active substances present comprise one or more builder materials, surfactants, bleach activators, enzymes, enzyme stabilizers, corrosion inhibitors, scale inhibitors, complexing agents, inorganic salts, graying inhibitors, foam inhibitors, silicone oils, soil release compounds, color transfer inhibitors, salts of polyphosphonic acids, optical brighteners, fluorescence agents, disinfectants, fragrances, dyes, antistats, easy-iron agents, repellants and impregnants, swelling and nonslip agents, UV absorbers, or mixtures thereof.

14. The process of claim 12, wherein the tablet is a machine dishwashing tablet and has a cavity.

15. The process of claim 13, wherein the tablet is a machine dishwashing tablet and has a cavity.

16. The process of claim 15, wherein the filling introduced into the cavity which comprise active substances which are released only in a wash cycle or rinse cycle after the actual cleaning of the ware.

17. The process of claim 16, wherein the active substances comprising the filling are released in the clear-rinse cycle.

18. The process of claim 17, wherein the active substances are one or more selected from the group consisting of surfactants, including rinse-aid surfactants, bleaches, bleach activators, corrosion inhibitors, scale inhibitors, fragrances and/or cobuilders.

19. The process of claim 12, wherein the tablet is a laundry detergent and has a cavity.

20. The process of claim 13, wherein the tablet is a laundry detergent and has a cavity.

21. The process of claim 20, wherein a filling is introduced into the cavity that comprises active substances that are not released until a wash cycle or rinse cycle after the actual washing of the textile.

22. The process of claim 21, wherein the active substances comprising the fillings are released in the clear-rinse cycle.

23. The process of claim 21, wherein the active substances are one or more selected from the group consisting of anionic, nonionic, cationic, amphoteric and zwitterionic surfactants, cationic and nonionic textile softeners, foam inhibitors, perfume oils, dyes, preservatives, soil release polymers, antistats, and easy-iron agents.

24. The process of claim 1, wherein the tablet comprises a disinfectant.

25. The process of 1, wherein the tablet comprises active cosmetic and pharmaceutical substances.

26. The process of claim 1, wherein the tablet comprises as active substance one or more adhesives.

27. The process of claim 26, wherein the one or more adhesives comprise a water-based adhesive.

28. The process of claim 26, wherein the tablet comprises wallpaper paste as adhesive.

29. The process of claim 1, wherein active substances present comprise chemical and biological fertilizers, pesticides, herbicides, components for water preparation, catalysts and fuels.

* * * * *